US009857290B2

(12) United States Patent
Albert et al.

(10) Patent No.: US 9,857,290 B2
(45) Date of Patent: Jan. 2, 2018

(54) TILTED GRATING SENSOR

(71) Applicant: Weatherford Canada Partnership, Calgary (CA)

(72) Inventors: Jacques Albert, Gatineau (CA); Chengkun Chen, Kanata (CA); Yanina Shevchenko, Ottawa (CA); Alexei Ivanov, Ottawa (CA)

(73) Assignee: WEATHERFORD CANADA LTD., Edmonton, Alberta (CA)

( * ) Notice: Subject to any disclaimer, the term of this patent is extended or adjusted under 35 U.S.C. 154(b) by 199 days.

(21) Appl. No.: 14/010,770

(22) Filed: Aug. 27, 2013

(65) Prior Publication Data
US 2014/0002821 A1 Jan. 2, 2014

Related U.S. Application Data

(62) Division of application No. 12/439,031, filed as application No. PCT/CA2006/001749 on Oct. 25, 2006, now Pat. No. 8,554,024.

(51) Int. Cl.
| G01N 21/21 | (2006.01) |
| G01B 11/16 | (2006.01) |
| G01N 21/552 | (2014.01) |
| G01N 21/77 | (2006.01) |
| G01N 33/543 | (2006.01) |
| G01D 5/353 | (2006.01) |

(52) U.S. Cl.
CPC ............. *G01N 21/21* (2013.01); *G01B 11/18* (2013.01); *G01D 5/35316* (2013.01); *G01N 21/553* (2013.01); *G01N 21/774* (2013.01); *G01N 33/54373* (2013.01); *G01N 2021/7776* (2013.01)

(58) Field of Classification Search
CPC .. G02F 2201/307; G02B 6/1226; G02B 6/124
USPC .......................................................... 385/10
See application file for complete search history.

(56) References Cited

U.S. PATENT DOCUMENTS

| 4,039,249 A | 8/1977 | Kaminow et al. |
| 5,071,248 A | 12/1991 | Tiefenthaler et al. |
| (Continued) | | |

FOREIGN PATENT DOCUMENTS

| CA | 2442972 | 11/2002 |
| CA | 2504765 | 10/2005 |
| (Continued) | | |

OTHER PUBLICATIONS

Kang et al. "Temperature-Independent Strain Sensor System Using a Tilted Fiber Bragg Grating Demodulator", IEEE Photonics Technology Letters, vol. 10, No. 10, Oct. 1998.*

(Continued)

*Primary Examiner* — Casey Bryant

(57) ABSTRACT

The present invention relates to a sensor using a tilted fiber grating to detect physical manifestations occurring in a medium. Such physical manifestations induce measurable changes in the optical property of the tilted fiber grating. The sensor comprises a sensing surface which is to be exposed to the medium, an optical pathway and a tilted grating in the optical pathway. The grating is responsive to electromagnetic radiation propagating in the optical pathway to generate a response conveying information on the physical manifestation.

4 Claims, 14 Drawing Sheets

(56) References Cited

U.S. PATENT DOCUMENTS

| | | | |
|---|---|---|---|
| 5,511,083 A | 4/1996 | D'Amato et al. | |
| 5,641,956 A * | 6/1997 | Vengsarkar | G02B 6/02095 250/227.14 |
| 5,848,204 A | 12/1998 | Wanser | |
| 6,058,226 A * | 5/2000 | Starodubov | G02B 6/02195 250/227.11 |
| 6,069,985 A * | 5/2000 | Albin | G01L 1/246 385/12 |
| 6,427,041 B1 * | 7/2002 | Strasser et al. | 385/37 |
| 6,490,078 B2 | 12/2002 | Enomoto et al. | |
| 6,776,962 B1 | 8/2004 | Boss et al. | |
| 6,839,131 B2 | 1/2005 | Kwon | |
| 6,891,651 B2 | 5/2005 | Kim et al. | |
| 6,965,708 B2 | 11/2005 | Luo et al. | |
| 7,127,139 B2 | 10/2006 | Onaka et al. | |
| 7,526,156 B2 | 4/2009 | Lee et al. | |
| 8,811,776 B2 * | 8/2014 | Zhou | G01K 11/3206 385/12 |
| 2001/0026396 A1 | 10/2001 | Enomoto et al. | |
| 2004/0174913 A1 | 9/2004 | Leplingard et al. | |
| 2004/0175074 A1 | 9/2004 | Dykaar | |
| 2004/0196537 A1 | 10/2004 | Starodoumov | |
| 2005/0147342 A1 | 7/2005 | Uchiyama et al. | |
| 2005/0185885 A1 | 8/2005 | Onaka et al. | |
| 2006/0013527 A1 | 1/2006 | Morel et al. | |
| 2006/0045422 A1 | 3/2006 | Provost et al. | |
| 2006/0067616 A1 | 3/2006 | Kanji et al. | |
| 2006/0187541 A1 | 8/2006 | Starodoumov | |
| 2008/0089644 A1 | 4/2008 | Lee et al. | |

FOREIGN PATENT DOCUMENTS

| | | |
|---|---|---|
| CA | 2526604 | 5/2006 |
| WO | WO 2004/032746 | 4/2004 |
| WO | WO 2004/092730 | 10/2004 |

OTHER PUBLICATIONS

International Search Report issued in PCT/CA2006/001749.
Written Opinion of the International Searching Authority issued in PCT/CA2006/001749.
S. C. Kang et al., "Temperature-Independent Strain Sensor System Using a Tilted Fiber Bragg Grating Demodulator", IEEE Photonics Technology Letters, vol. 10, No. 10, Oct. 1998, pp. 1461-1463.
Y. Y. Shevchenko et al., "Plasmon Resonances in Gold-Coated Tilted Fiber Bragg Gratings", Department of Electronics, Carleton University, Ottawa, Ontario, Canada, 14 pages.
C. Chen et al., "Differential Sensitivity Characteristics of Tilted Fiber Bragg Grating", Department of Electronics, Carleton University, Ottawa, Canada, 10 pages.
C. Chen et al., "Stain-Optic Coefficients of Individual Cladding Modes of Singlemode Fibre: Theory and Experiment", Electronic Letters, Aug. 31, 2006, vol. 42, No. 18, 2 pages.

\* cited by examiner

TILTED GRATING SENSOR

This application is a divisional of U.S. patent application Ser. No. 12/439,031, filed on Feb. 26, 2009, now U.S. Pat. No. 8,554,024, which is the U.S. national stage of PCT/CA06/01749, filed on Oct. 25, 2006. All of the above applications are herein incorporated by reference in their entirety.

FIELD OF THE INVENTION

The invention relates to a sensor using a tilted fiber grating to detect external events that induce measurable changes in an optical property of the tilted fiber grating. The sensor can be used to sense a wide range of biological processes, biological elements, chemical elements or manifestations of physical phenomena such as temperature, strain or index of refraction.

BACKGROUND OF THE INVENTION

Fiber Bragg grating (FBG) sensors have a wide range of applications such as pressure-strain sensors, temperature sensors, micro-bending sensors and external refractive index sensors. As these optical sensors are inherently immune from electromagnetic interference and chemically inert, they are very attractive in bio-chemical applications and hazardous surroundings.

The sensing mechanism most often used in FBGs arises from the fact that the reflection wavelength for the forward propagating core mode varies linearly with temperature and strain. Since the wavelength can be measured with an accuracy of 10 pm relatively easily near 1550 nm, this represents a relative resolution of about 6 ppm. A variant of the same concept uses so-called Long Period Gratings (LPG) where coupling occurs between the forward propagating core mode and forward propagating cladding modes. In this case, the sensitivity of the resonance wavelength to perturbations can be greatly enhanced for some of the cladding modes. Furthermore, since LPGs involve cladding modes there has been great interest in using these for refractive index sensing by immersing the fibers in the medium to be measured. Special absorbing coatings can also be used to detect chemicals or liquids through the refractive index changes (or volume changes) induced in the coatings. However, the spectral response of LPG resonances is rather broad (width greater than 10 nm) making high accuracy measurements of small wavelength changes more difficult than with FBGs. Ideally, such refractive index sensors should be able to distinguish different kinds of perturbations, and insensitivity to temperature is often particularly desirable. A problem with both FBG and LPG sensors is that they are intrinsically quite sensitive to temperature, with resonance wavelengths drifting by about 10 pm/°C, unless special bulky packaging is used to athermalize the device. In order to circumvent this problem in refractive index sensors, devices proposed so far have involved combination of gratings in one sensor such as two different types of fiber Bragg gratings, two fiber Bragg gratings with different cladding diameters and a long period grating (LPG) with a Bragg gratings. In such cases, the differential sensitivity of the two gratings to temperature and the desired measurand is used to discriminate between the two perturbations.

Against this background it can be clearly seen that the current sensor technology has drawbacks. It is therefore the aim of the present invention to alleviate those drawbacks.

SUMMARY OF THE INVENTION

As embodied and broadly described herein the invention provides a sensor for sensing at least one physical manifestation occurring in a medium. The sensor comprises a sensing surface for exposure to the medium, an optical pathway and a tilted grating in the optical pathway. The grating is responsive to electromagnetic radiation propagating in the optical pathway to generate a response conveying information on the at least one physical manifestation.

As embodied and broadly described herein the invention also provides a sensor for sensing a physical manifestation occurring externally of the sensor. The sensor comprises a sensing surface for exposure to the physical manifestation, an optical pathway and a tilted grating in the optical pathway. The tilted grating is responsive to electromagnetic radiation propagating in the optical pathway to induce SPR adjacent the sensing surface.

As embodied and broadly described herein the invention also provides a method for detecting the presence of bacteria in a medium. The method comprises providing a sensor having a sensing surface, the sensor also having an optical pathway containing a tilted grating, placing the sensing surface in contact with the medium and determining from a response of the sensor if the bacteria is present in the medium.

As embodied and broadly described herein the invention also provides a method for detecting the presence of virus in a medium. The method comprises providing a sensor having a sensing surface, the sensor having an optical pathway containing a tilted grating, placing the sensing surface in contact with the medium and determining from a response of the sensor if the virus is present in the medium.

As embodied and broadly described herein the invention also provides a method for measuring the concentration of sugar in a medium. The method comprises providing a sensor having a sensing surface, the sensor having an optical pathway containing a tilted grating, placing the sensing surface in contact with the medium and determining from a response of the sensor the concentration of sugar in the medium.

As embodied and broadly described herein the invention also provides a method for measuring the concentration of alcohol in a medium. The method comprises providing a sensor having a sensing surface, the sensor having an optical pathway containing a tilted grating, placing the sensing surface in contact with the medium and determining from a response of the sensor the concentration of alcohol in the medium.

As embodied and broadly described herein the invention also provides a method for detecting the presence of a chemical or biological element in a medium. The method comprises providing a sensor having a sensing surface, the sensor having an optical pathway containing a tilted grating, placing the sensing surface in contact with the medium and determining from a response of the sensor if the chemical or biological element is present in the medium.

As embodied and broadly described herein the invention also provides a method for measuring a degree of curing of a curable material. The method comprises the steps of providing a sensor having a sensing surface, the sensor having an optical pathway containing a tilted grating, placing the sensing surface in contact with the curable material determining from a response of the sensor the degree of curing of the curable material.

As embodied and broadly described herein the invention also provides an elongation strain sensor. The elongation strain sensor comprises an optical pathway and a tilted grating in the optical pathway to generate a response conveying information on elongation strain acting on the sensor.

As embodied and broadly described herein the invention also provides a method for measuring elongation strain. The method comprises receiving a response from a sensor containing a tilted grating subjected to elongation strain, the response conveying information on reaction of the tilted grating to elongation strain and on reaction of the tilted grating to temperature, processing the response of the tilted grating to distinguish the reaction of the tilted grating to elongation strain from the reaction of the tilted grating to temperature.

As embodied and broadly described herein the invention also provides an apparatus for measuring elongation strain. The apparatus comprises an elongation strain sensor having an optical pathway, a tilted grating in the optical pathway to generate a response conveying information on elongation strain and temperature acting on said sensor and a signal processing unit to process the response of the tilted grating and distinguish in the response to reaction of the tilted grating to elongation strain from the reaction of the tilted grating to temperature.

As embodied and broadly described herein the invention also provides a bending strain sensor. The bending strain sensor comprises an optical pathway and a tilted grating in the optical pathway to generate a response conveying information on bending strain acting on the sensor.

As embodied and broadly described herein the invention also provides a method for measuring bending strain. The method comprises receiving a response from a sensor containing a tilted grating subjected to bending strain, the response conveying information on: reaction of the tilted grating to bending strain; reaction of the tilted grating to temperature. The method also comprises processing the response of the tilted grating to distinguish the reaction of the tilted grating to bending strain from the reaction of the tilted grating to temperature.

As embodied and broadly described herein the invention also provides an apparatus for measuring bending strain. The apparatus comprises a bending strain sensor, having an optical pathway, a tilted grating in said optical pathway to generate a response conveying information on bending strain and temperature acting on said tilted grating, a signal processing unit to process the response of the tilted grating and distinguish in the response to reaction of said tilted grating to bending strain from the reaction of the tilted grating to temperature.

As embodied and broadly described herein the invention also provides a pressure sensor. The pressure sensor comprises an optical pathway, a tilted grating in the optical pathway to generate a response conveying information on bending strain acting on said sensor, a flexible member, the optical pathway being mounted to the flexible member. The flexible member flexes in response to pressurized fluid and induces in the tilted grating bending strain.

As embodied and broadly described herein the invention also provides a sensor, for sensing at least one physical manifestation occurring in a medium. The sensor comprises an optical pathway an interface coupled with the optical pathway, the interface being responsive to the physical manifestation to induce strain on said optical pathway; a tilted grating in the optical pathway, the tilted grating being responsive electromagnetic radiation propagating in the optical pathway to generate a response conveying information on the strain induced on the optical pathway.

BRIEF DESCRIPTION OF THE DRAWINGS

A detailed description of examples of implementation of the present invention is provided hereinbelow with reference to the following drawings, in which.

Figure 1A:
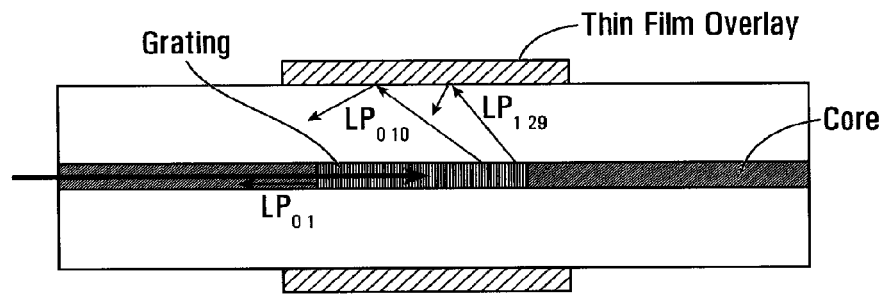
FIG. 1a is a high level schematic of a TFBG sensor.

In the drawings, embodiments of the invention are illustrated by way of example. It is to be expressly understood that the description and drawings are only for purposes of illustration and as an aid to understanding, and are not intended to be a definition of the limits of the invention.

DETAILED DESCRIPTION

A non-limiting example of implementation of this invention uses an optical structure in which light is guided by a core medium able to support one or few guided modes, surrounded by a finite-sized cladding medium whereas the cladding itself acts as a multimode waveguide. Specific examples of this structure include optical fibers and planar light circuit (PLC). In a weakly tilted fiber Bragg grating (TFBG) sensor both a core mode resonance and several cladding mode resonances appear simultaneously, as shown in FIG. 1. Weakly tilted gratings are defined as having a tilt angle greater than zero but less than 45 degrees relative to the propagation axis, so that there is a non-zero core mode reflection induced by the grating. In a specific example, the tilt angle is in the range from greater than zero and about 20 degrees. In a more specific example the tilt angle is in the range from about 2 degrees to 12 degrees. This has several advantages. The cladding mode resonances are sensitive to the external environment (refractive index, deposited layer thicknesses, etc.) and to physical changes in the whole fiber cross-section (shear strains arising from bending for instance), while the core mode (Bragg) resonance is only sensitive to axial strain and temperature. The temperature dependence of cladding modes is similar to that of the core modes, so that the effect of temperature can be removed from the cladding mode resonance by monitoring the wavelength difference between the core mode resonance and selected cladding mode resonances. Using this technique, sensors can be made for sensing physical manifestations such as elongation strain, bending, or measuring the Surrounding Refractive Index (SRI), that are temperature-independent.

Another feature which may constitute an advantage of the TFBG over the LPG to couple to cladding modes is that the resonances are as narrow as those of a FBG, i.e. of the order of a few hundred pm, instead of several tens of nm for LPGs. Therefore, wavelength interrogation for TFBG occurs over narrow wavelength ranges and makes it possible to use commonly available light sources, detectors, couplers and multiplexers. In particular, a typical entire TFBG spectrum fits easily within the standard telecommunication bands (1530-1560 nm). Also, by using the resonance positions and/or strengths individually, allows extracting multiple sensing parameters from a single sensor. More specifically, a multi-functional sensor can be built by monitoring several cladding mode resonances (or groups of resonances) which have different sensitivities to different physical manifestations. For instance, bending affects mainly low order cladding modes, while SRI variations affect higher order cladding modes preferentially, and neither perturbation affects the core mode resonance.

As is well known, the Bragg reflection and cladding mode resonance wavelengths $\lambda B$ and $\lambda iclad$ of TFBG are determined by a phase-matching condition and can be expressed as follows:

$$\lambda_B = 2n_{eff}\Lambda/\cos\theta \quad (1)$$

$$\lambda^i_{clad} = (n^i_{eff} + n^i_{clad})\Lambda/\cos\theta \quad (2)$$

where neff, nieff and niclad are the effective indices of the core mode at $\lambda B$ and the core mode and the ith cladding mode at $\lambda iclad$ respectively, and $\Lambda$ and $\theta$ are the period and the internal tilt angle of the TFBG. The tilt angle is defined as the angle formed by the TFBG and the imaginary axis of the optical pathway containing the TFBG along which the optical signal interrogating the TFBG propagates. When the optical pathway is defined by an optical fiber, the axis of the optical fiber will usually constitute the axis of optical signal propagation. For TFBG structures, if only the Bragg and cladding mode wavelength shifts ($\Delta\lambda B$, $\Delta\lambda iclad$) caused by external refractive index changes ($\Delta next$) and temperature changes ($\Delta T$) are taken into account, the wavelength shifts $\Delta\lambda B$ and $\Delta\lambda iclad$ can be written from equations (1) and (2) as follows:

In standard optical fibers, the effective index of core modes ($n_{eff}$, $n^i_{eff}$) are insensitive to the external refractive index changes, so the equations (3) and (4) may be simplified as following:

Equations (5) and (6) show that the cladding resonances will change with the external refractive index, but not the Bragg wavelength. It can also be seen that the different cladding modes may have different sensitivities to SRI changes. The differential wavelength shift, which can be used as a sensing quantity, is given by Equation (7). The second term on the right-hand-side of Equation (7) represents the temperature dependence of the relative wavelength shift. Using the thermal expansion coefficient of silica ($0.55 \times 10^{-6}/°$ C.) and an extreme worst case estimate of $1 \times 10^{-6}/°$ C. for the difference in the temperature dependence of the refractive indices of the core and cladding glasses (which change individually by about $10 \times 10^{-6}/°$ C.)), it can be shown that the temperature dependence of the differential resonance is less than 0.54 pm/° C. for the differential wavelength shift.

Accordingly, the value of $\Delta n_{ext}$ determined from Equation (7) is the value for the SRI at the sensing temperature (and the temperature can be determined independently by the core mode resonance value from Equation (5)).

A number of simulations of TFBG constructions will now be discussed to illustrate the main features of the TFBG sensor. Those simulations have been made using a commercial optical fiber grating software simulator, such as Opti-Grating version 4.2 from Optiwave Corp., (http://www.optiwave.com).

First, a TFBG with grating period of 534 nm and internal tilt angle of 4.5° was simulated in a CORNING SMF-28 standard optical fiber as a function of the refractive index of the external medium (SRI). The structure of such TFBG grating is shown at FIG. 1a. Broadly speaking, the TFBG is integrated into an optical pathway 10 which is in the form of an optical fiber. The optical pathway has a core 12 surrounded by a cladding 14. The TFBG grating 16 is written into the core 12. The axis of the TFBG 16, which is perpendicular to the bars forming the grating 16 is at an angle of 4.5° with relation of the axis 18 of the optical pathway 12, along which an optical signal interrogating the TFBG 16 propagates. When the TFBG 16 is interrogated by an optical signal the TFBG 16 produces a response that has two components. One of the components is the core mode resonance 20 which is reflected back toward the source of the optical signal. The other is the cladding mode resonance 22 which includes a series of individual emissions at different wavelengths that propagate in the cladding 14 toward the outer surface of the optical pathway.

Figure 1B:
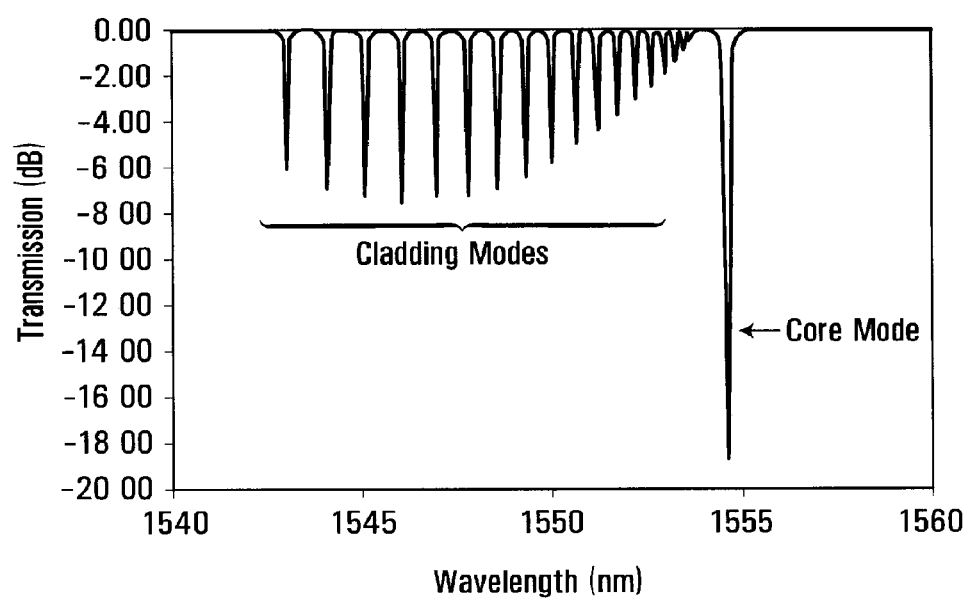
FIG. 1b is a graph showing the simulated transmission spectrum of a TFBG.
Figure 2A:
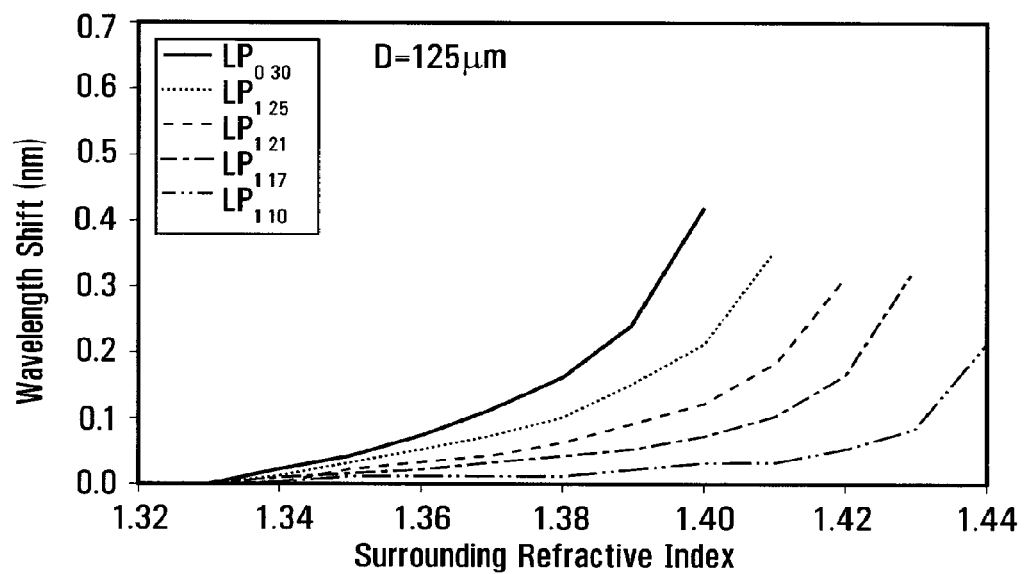
FIG. 2a is a graph showing the differential wavelength shift for selected TFBG resonances as a function of the refractive index of the surrounding medium for a 125 μm cladding diameter.

FIG. 2(a) shows the wavelength shift of 5 different cladding mode resonances (relative to the core mode resonance, which remains fixed) when the SRI changes from 1.33 to 1.44. The highest order cladding modes begin to shift sooner as the SRI increases because their mode field intensity extends further into the external medium as they are closer to their cut-off. High order modes sequentially disappear (from the short wavelength side, as shown in FIG. 1b) when the SRI reaches values for which they are cut-off.

Note that the final slope before cut-off for the various resonances appears to converge for all the modes to a common value near 180 pm/% SRI. Therefore, monitoring several resonances simultaneously allows high sensitivity measurements of SRI over a larger range of values.

Figure 2B:
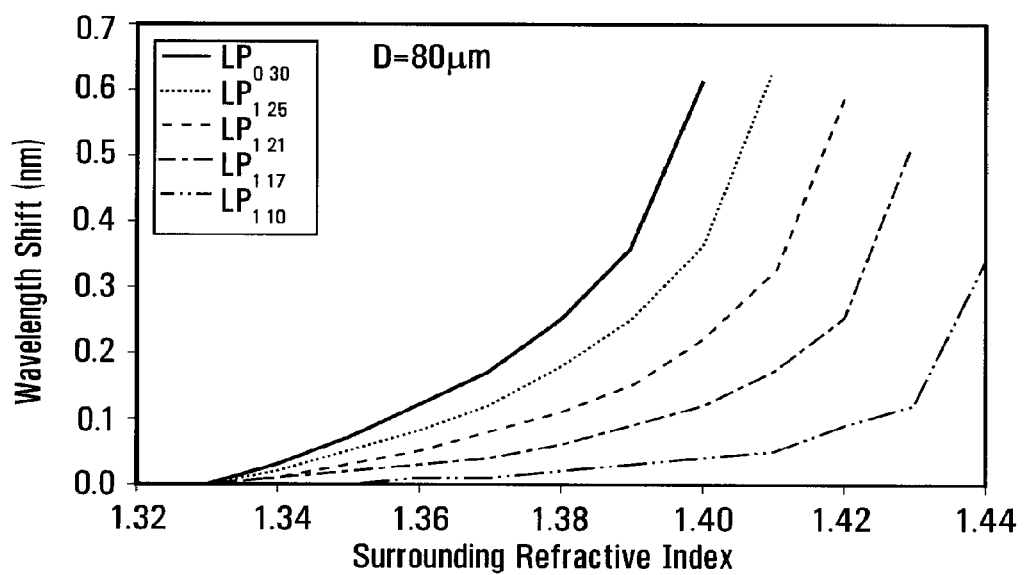
FIG. 2b is a graph showing the differential wavelength shift for selected TFBG resonances as a function of the refractive index of the surrounding medium for an 80 μm cladding diameter.

Higher sensitivity also can be achieved by reducing the cladding layer thickness (by etching in diluted hydrofluoric acid for instance), or by using fibers that are fabricated with smaller diameter claddings: this results in fewer cladding modes that are more widely separated in wavelength. If the cladding layer diameter is reduced from 125 µm to 80 µm, the SRI sensitivity becomes 350 pm/% SRI, as shown in FIG. 2(b). By further reducing the cladding layer diameter, much higher wavelength shifts can be expected. Note that a potential problem may arise if the cladding layer diameter is reduced to less than 30 µm; at or near this value the Bragg wavelength becomes sensitive to the SRI changes and the in-fiber temperature reference may be lost. Another option is to use functional thin films to "pull" certain modes out of the fiber cladding and make them sensitive to specific environments.

Figure 3:
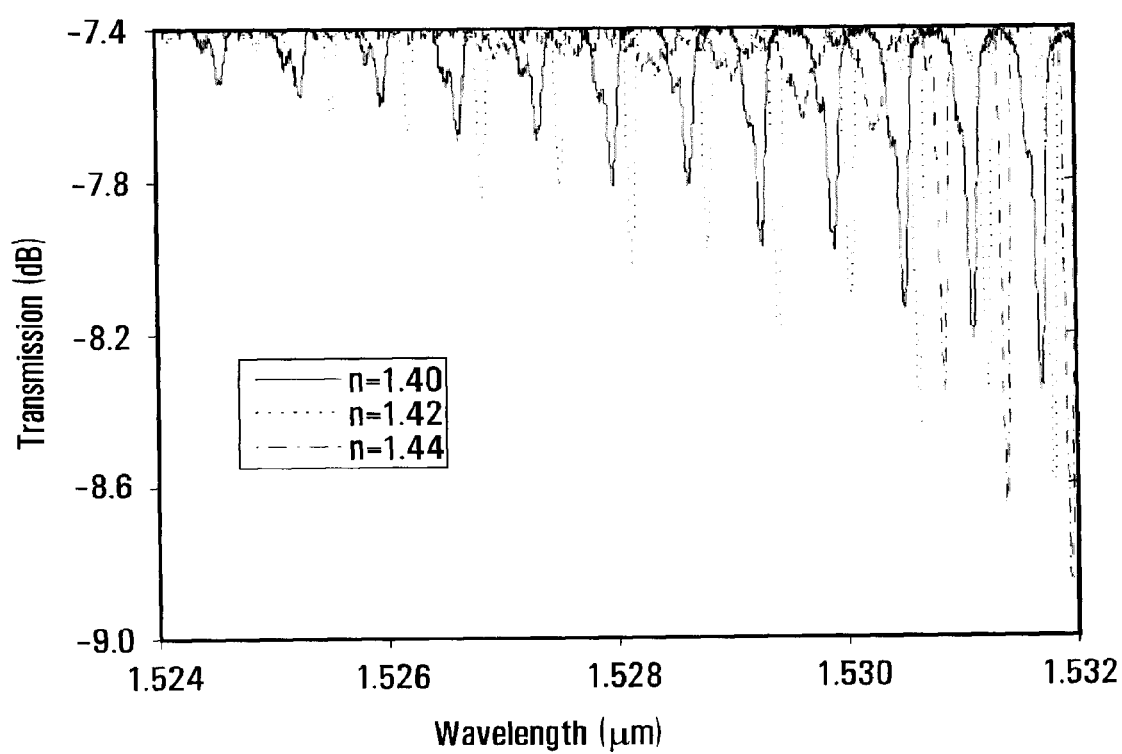
FIG. 3 is a graph showing the experimental TFBG transmission spectrum for three values of SRI.
Figure 4:
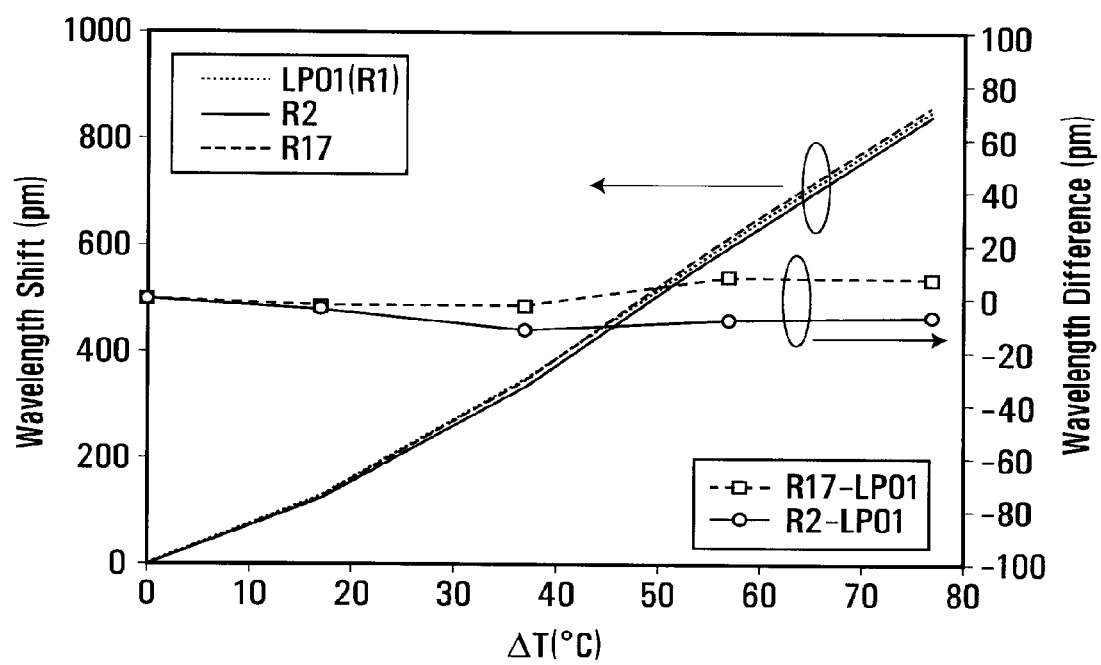
FIG. 4 is a graph showing the temperature sensitivity of several TFBG resonances and differential shift from the core mode resonance.

The results of experimental work conducted for SRI sensing and temperature insensitivity are shown in FIGS. 3 and 4 respectively. The TFBG is written in a CORNING SMF 28 fiber using ArF excimer laser light at 193 nm and a phase mask to generate the grating pattern. This is not to be considered a restriction since any method of fabrication for FBGs is applicable to the sensors described here. The tilt angle was adjusted experimentally until the core and main cladding mode resonance transmission dips achieved comparable attenuation levels. The exact value of the tilt angle is not a critical parameter as it only influences the relative strengths of the core and cladding mode resonances for a given sensor (and hence only impacts the details of the sensor interrogation scheme chosen in a particular case). The SRI sensitivity was obtained by measuring the transmission spectra of the TFBG immersed in calibrated refractive index fluids (from Cargille Laboratories). FIG. 3 shows the changes in transmission of the highest order cladding modes with SRI of 1.40, 1.42 and 1.44, illustrating that resonance shifts increase with mode order and that large changes occur when modes approach cut-off.

The measured wavelength shifts of modes approaching cut-off are 0.275 nm and 0.218 nm when the SRI changes from 1.40 to 1.42 and 1.42 to 1.44 respectively. The latter shift corresponds to a sensitivity of 300 pm/% SRI, actually higher than the theoretical values indicated previously. If the power level within a narrow band at a fixed wavelength is monitored instead of the wavelength itself, the above mentioned wavelength sensitivity translates into a change in transmitted power of 20% for a change in SRI of 0.7% since resonances are at most 200 pm wide for 1 cm-long gratings, and several resonances have an amplitude of about 1 dB. By monitoring simultaneously the power level near the core mode resonance and assuming that 0.1% level difference between the two measurements can be detected, the minimum detectable SRI is of the order of $4 \times 10^{-5}$. It is important to note that the first resonance on the short wavelength side of the core mode Bragg reflection is a ghost mode which does not appear in simulations unless a UV induced break in symmetry or relatively large core index increase is included in the calculation. This ghost mode may be useful in detection of fiber bends and shear stresses.

As mentioned above, it is desirable that the wavelength shifts measured in SRI sensing do not depend on the temperature of the sensor. The experiments show that while individual resonances of core and selected cladding modes each drift by ~10 pm/° C. (for the first resonance ($LP_{01}$: Bragg wavelength resonance), the second resonance (ghost mode resonance) and the seventeenth resonance), as shown in FIG. 4, the relative wavelength shift between the cladding modes and the Bragg wavelength is less than 0.4 pm/° C. This represents a ~27 times reduction in sensitivity from the resonance wavelengths themselves.

This confirms the usefulness of the self-referencing feature for making this SRI sensor temperature-independent.

Figure 5:
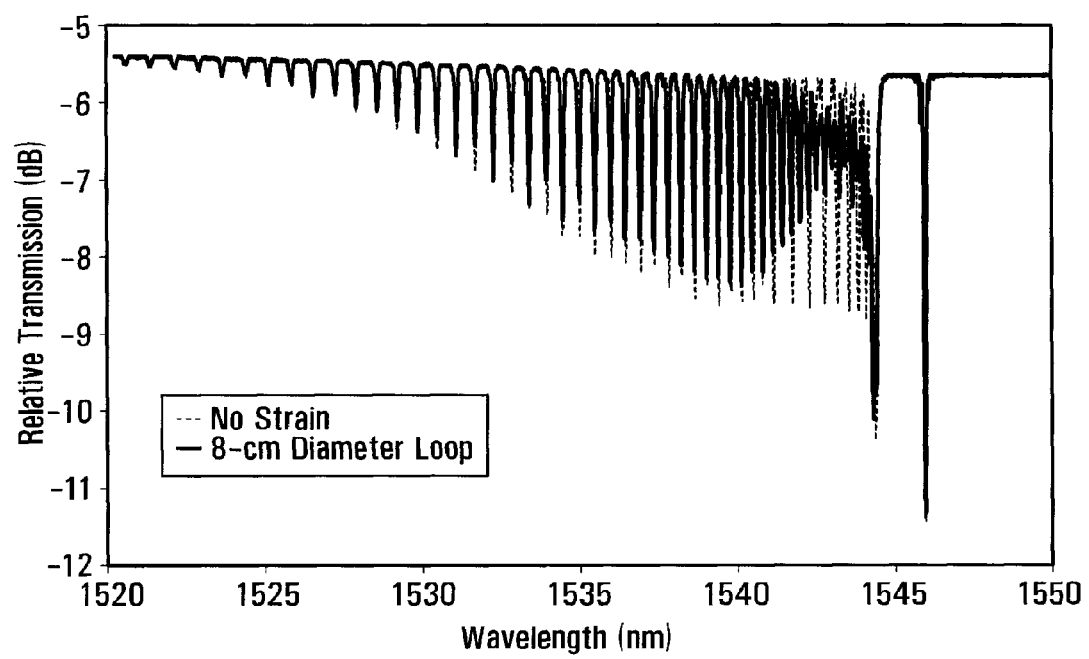
FIG. 5 is a graph showing the effect of bending of a TFBG on its transmission spectrum.

Finally, the experimental results show that the TFBG spectrum changes as a function of bending in FIG. 5 (using a stronger grating written in hydrogen-loaded fiber). As expected since the fiber core lies on a neutral strain axis for pure bending, the core mode resonance and high order cladding modes remain unchanged but the first few low order cladding mode resonances change by several dB for the bending radii tested. Therefore, a single sensor can be used to detect three different physical manifestations simply by interrogating it over three different wavelength ranges: 1) near the Bragg resonance for temperature; 2) near low order cladding modes for bending; 3) at the short wavelength end of the transmission spectrum for SRI.

A particularly simple interrogation scheme for the TFBG could be constructed by spectrally slicing the transmitted light using an arrayed waveguide grating (AWG) butt-coupled to a detector array. The spacing and widths of the resonances are quite compatible with standard 40 or 80 channels AWGs that are widely available from telecommunications component vendors. Instead of tracking wavelength shifts, the detectors monitor power level changes at fixed wavelength positions. One channel of the AWG interrogator can be used in closed loop to thermally tune the AWG (forcing its wavelength comb to follow the core mode resonance) while the output of another channel would reveal the power level changes associated with the relative wavelength shift of a cladding mode resonance. Level discretization and digital processing can then be used to extract meaningful data from the TFBG response. For more information on this interrogation scheme, the reader is invited to refer to the article of G. Z. Xiao, P. Zhao, F. G. Sun, Z. G. Lu, Z. Zhang, and C. P. Grover, "Interrogating fiber Bragg grating sensors by thermally scanning a demultiplexer based on arrayed waveguide gratings," Opt. Lett., vol. 29, pp. 2222-2224, 2004. The content of this article is incorporated herein by reference.

Figure 6:
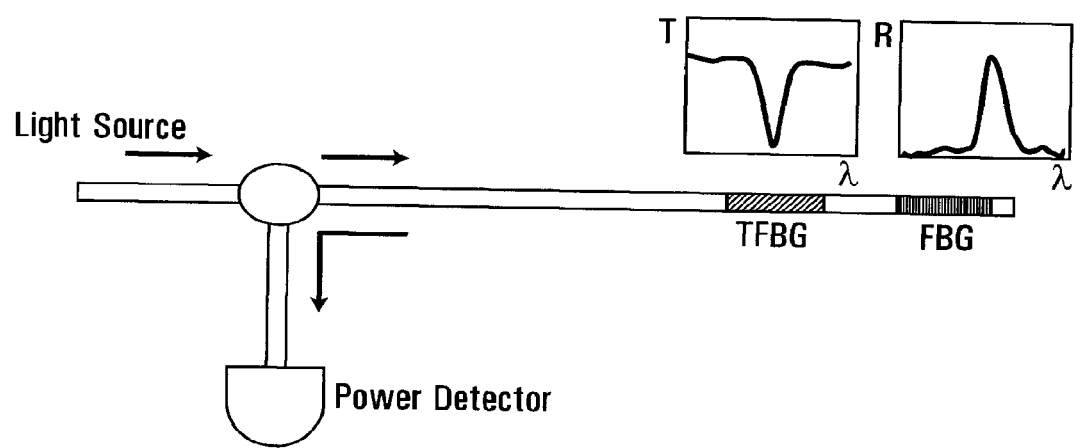
FIG. 6 is a scheme for interrogating an individual cladding mode resonance using a photo-detector collecting all the reflected light. The insets in the figure indicate the transmission spectrum of a typical TFBG (near a cladding mode resonance) and the reflection spectrum of the interrogating Fiber Bragg Grating (FBG). The position of the FBG reflection peak determines which cladding mode is interrogated.
Figure 7:
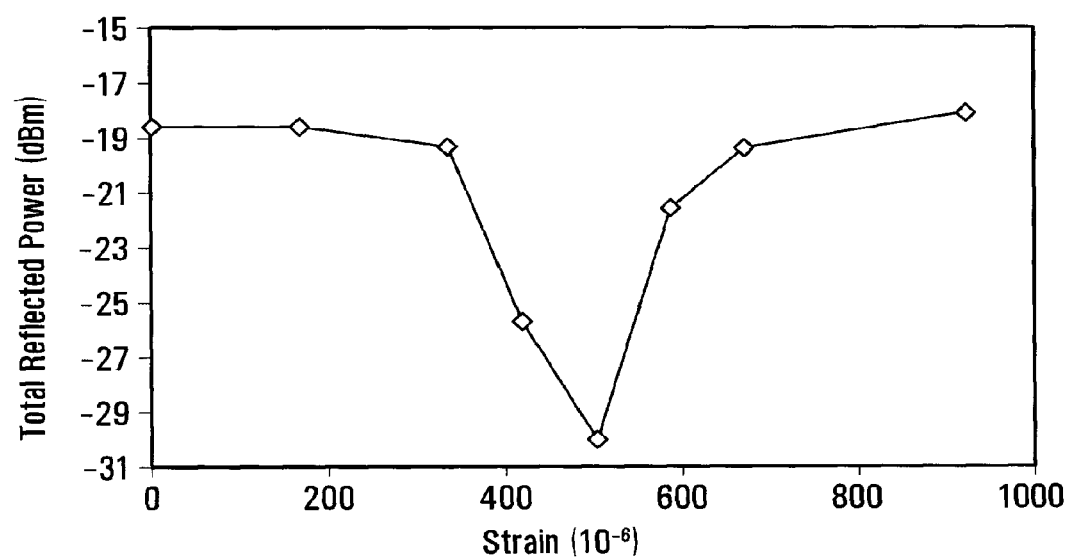
FIG. 7 is a graph showing the displacement of the reflected power from a TFBG-FBG pair when the FBG is tension-tuned across a TFBG cladding mode resonance.

Another scheme, requiring only a power detector, may be used to interrogate a selected cladding mode resonance independently of temperature or strain. This involves a pair of gratings as shown in FIG. 6. The TFBG is placed at the sensing point and is followed by a high reflectivity regular FBG of the same length (hence having the same spectral bandwidth) but with a Bragg wavelength λB centered near anyone of the cladding mode resonances (referred to as λC). Incident broadband light goes through the TFBG and gets attenuated at λC, continues to the FBG, gets reflected and returns towards after having passed a second time through the attenuating TFBG. This reflected light is recuperated from the fiber using either a circulator or a 3 dB coupler. The spectral bandwidth of the input light needs only to be large enough to cover the maximum wavelength excursion of the sensor in operation. The total amount of light reaching the detector consists of the residual Bragg reflection from the TFBG (which can be minimized for certain tilt angles) and the light reflected at λB. When λC=λB, very little light reaches the detector but as soon as the cladding mode resonance shifts or changes its strength the power level at the detector changes. As an example, such a pair of gratings were fabricated with λC>λB initially and then the FBG was stretched (thereby increasing λB) through the cladding mode resonance. Light from a pumped erbium-doped fiber broadband source was launched into the fiber containing the two gratings through a 3 dB coupler. The reflected power detected near the input of the fiber as a function of strain on the FBG is shown in FIG. 7. The graph shows that the power changes by more than 10 dB when λB becomes equal to λC. This represents a simple scheme to detect changes in Bragg wavelength or coupling strength without the need for an optical spectrum analyser. As shown in FIG. 4, if the two gratings illustrated in FIG. 6 are at the same temperature then λC and λB will move together and no power level change will be observed in the reflected signal. In most practical applications it would be the FBG that would provide the reference and the power level fluctuations would reflect changes in the TFBG cladding modes due to external perturbations. However the scheme is symmetrical with respect to the two gratings and the experimental results discussed here show that the sensitivity can be quite significant (0.1 dB/μStrain).

Figure 9:
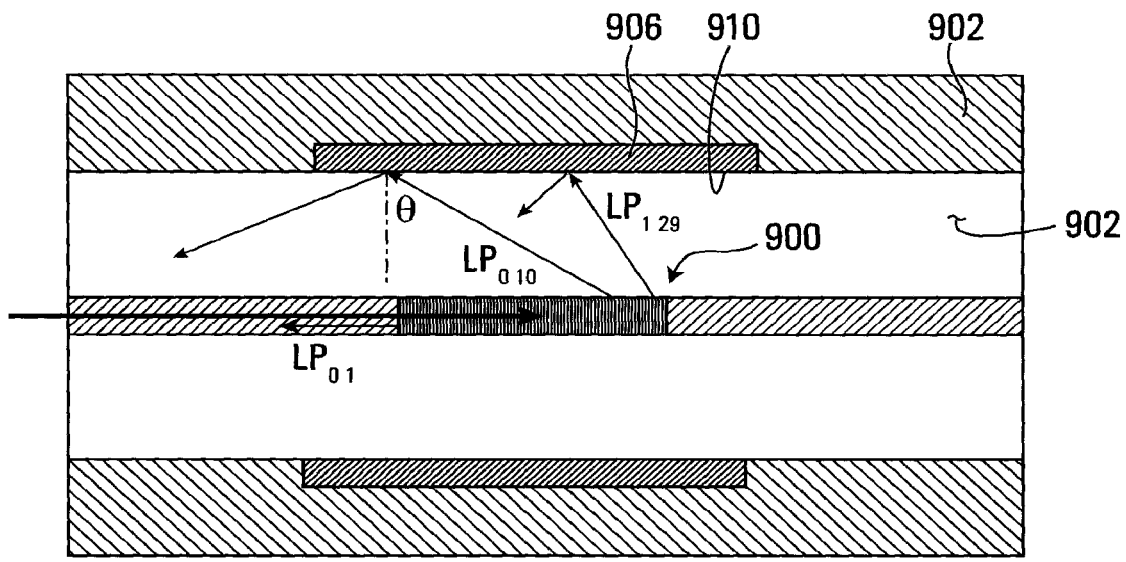
FIG. 9 is a cross-sectional view of optical fiber containing a TFBG that produces surface plasmon resonances.

In a possible variant, the TFBG is designed to produce plasmon resonances to perform measurements on physical manifestations. A typical setup is shown in FIG. 9. The TFBG 900 is fabricated in an optical fiber 902. The cladding 904 of the optical fiber 902 is coated with a suitable metal layer 906, such as gold to produce a dielectric/conductor interface 910. Such dielectric/conductor interface 910 gives rise to surface plasmon resonances. Specifically, in order for plasmon resonances to occur, the optical field within the fiber 802 has to have non zero amplitude at the dielectric/conductor interface 910 and a specific value of axial propagation constant (or, if one considers the ray optics approach to wave guiding, of angle of incidence within the total internal reflection regime).

Figure 8:
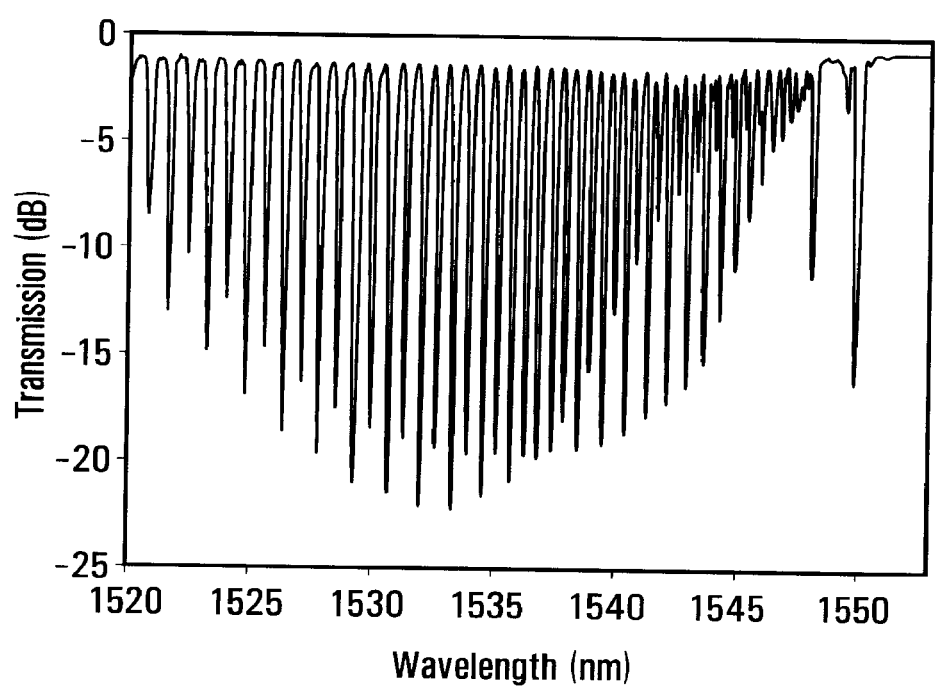
FIG. 8 is a graph showing the transmission spectrum of a TFBG.
Figure 10:
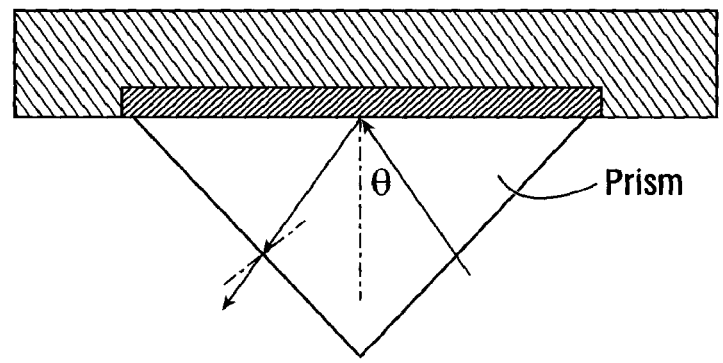
FIG. 10 shows a dielectric/conductor interface on an optical fiber to illustrate the Kretchman configuration for exciting SPR.

There are many potential applications for such structures, especially in the optical sensing of chemicals, among others. The TFBG 900 is used to couple the core mode light to a multitude of cladding modes, depending on the light wavelength, as shown in FIG. 8. The cladding modes have non-zero evanescent fields extending outside the cladding diameter and hence into the metal layer 906. When the axial component of the propagation constant of the cladding mode equals that of an SPR wave, coupling to that SPR wave can occur. A single TFBG is sufficient to generate a wavelength dependent set of cladding modes that are "interrogating" the metal layer 906 at various angles of incidence. This is most easily seen from the phenomenological representation shown in FIG. 9. FIG. 9 illustrates the ray optic analogy of the coupling from a guided core mode to several cladding modes through a TFBG. Each of the modes can be individually "addressed" simply by changing the wavelength of the guided light, and each mode strikes the cladding boundary at a different angle of incidence. On the other hand, FIG. 10 shows the traditional attenuated total reflection method (usually referred to as the Kretschmann configuration) to excite and detect SPR waves by changing the angle of incidence of the light beam incident on the metal film.

If there are non-radiative SPR waves that can be guided by the metal film surrounded on one side by silica glass and on the other side by a suitable medium, and if these SPR waves have an effective index (along the axis of the fiber) that is phase matched to one of the cladding modes effective indices, then coupling can occur between this cladding mode and the SPR wave. When this occurs, the cladding modes involved will experience more loss than their neighbours. The effective index of the $i^{th}$ cladding mode ($n^i_{clad}$), can be calculated from the resonance position $\lambda^i_{clad}$ by the following expression:

$$\lambda^i_{clad}=(n^i_{eff}+n^i_{clad})\Lambda/(\cos\theta) \quad (1)$$

where $n^i_{eff}$ is the effective index of the core mode at $\lambda^i_{clad}$, and $\Lambda$ and $\theta$ are the period and the internal tilt angle of the TFBG. The wavelengths of the cladding mode resonances that are perturbed as a result of a coupling to a SPR wave in a metal-coated TFBG, such as the TFBG 900, the provide a direct measure of the effective index of the SPW through Equation (1).

In the course of experimental work fiber gratings were fabricated using the standard process of KrF excimer laser irradiation of hydrogen-loaded CORNING SMF28 fiber through a phase mask. The required tilt was achieved by rotating the mask-fiber assembly around an axis perpendicular to the fiber axis and to the plane of incidence of the laser light. The transmission spectrum of the grating used for the experiments reported is shown in FIG. 8. The longest wavelength resonance corresponds to the reflection of the core mode light onto itself (Bragg wavelength), while all the shorter wavelength resonances correspond to the excitation of backward propagating cladding modes. These modes are not reflected back to the source because they are rapidly attenuated by the fiber jacket as soon as they leave the grating region (where the jacket has been removed prior to fabricating the grating). For resonances between 1520 and 1560 nm, phase mask periods of the order of 1 μm are used. After fabrication, the gratings were heat-stabilized by subjecting them to a rapid annealing at ~300° C. and the remaining hydrogen removed by 12 hours of heating at 120° C. prior to gold deposition. In these preliminary experiments, we used a small-scale sputtering chamber (Polaron Instruments model E5100) with the fiber positioned a few cm from the gold target. For flat samples in the same geometry, a gold layer thickness of 20 nm requires 1 minute of deposition at a pressure of 0.1 Torr, a potential difference of 2.5 kV, and 18-20 mA of sputter current. In order to coat the fiber as uniformly as possible, two coating runs were made with the fiber holder rotated by 180 degrees between the coatings. Under these conditions, the film uniformity around the fiber circumference is unlikely to be optimal. The film thickness on the fiber that is indicated in this specification is the value expected for the two sides of the fiber that directly facing the sputtering target during the two coating runs. While thicknesses ranging from 10 to 50 nm were tested, the following description will focus on results obtained with a 20 nm-thick nominal gold layer.

Figure 11:
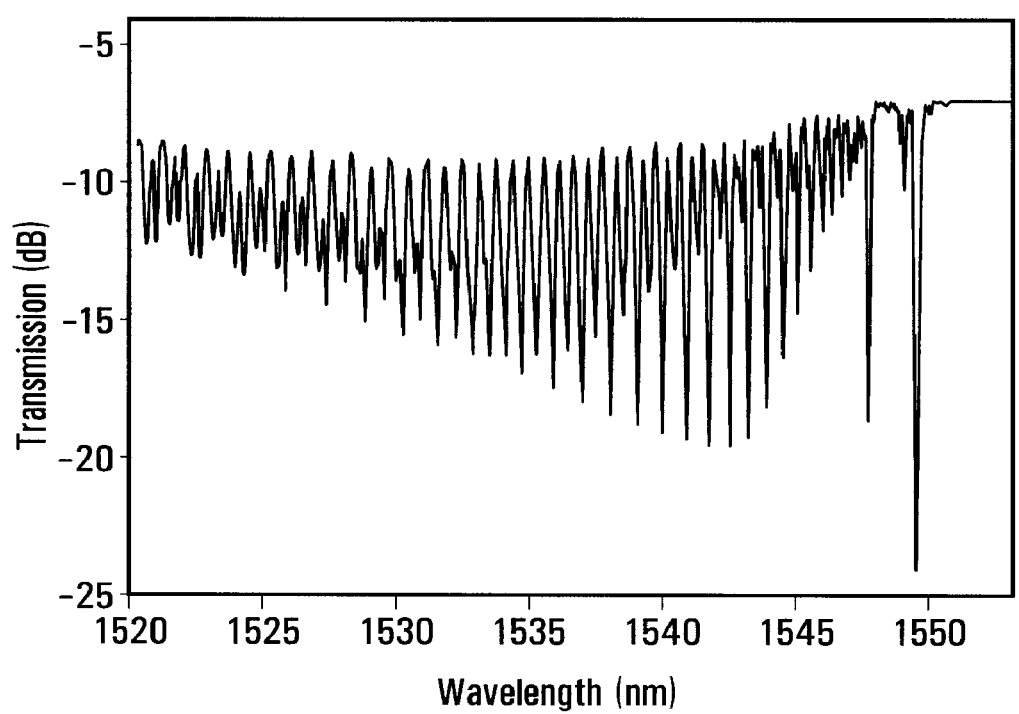
FIG. 11 is a graph illustrating the transmission spectrum of the same grating as the one of FIG. 8, but with a 20 nm gold layer in air.
Figure 12:
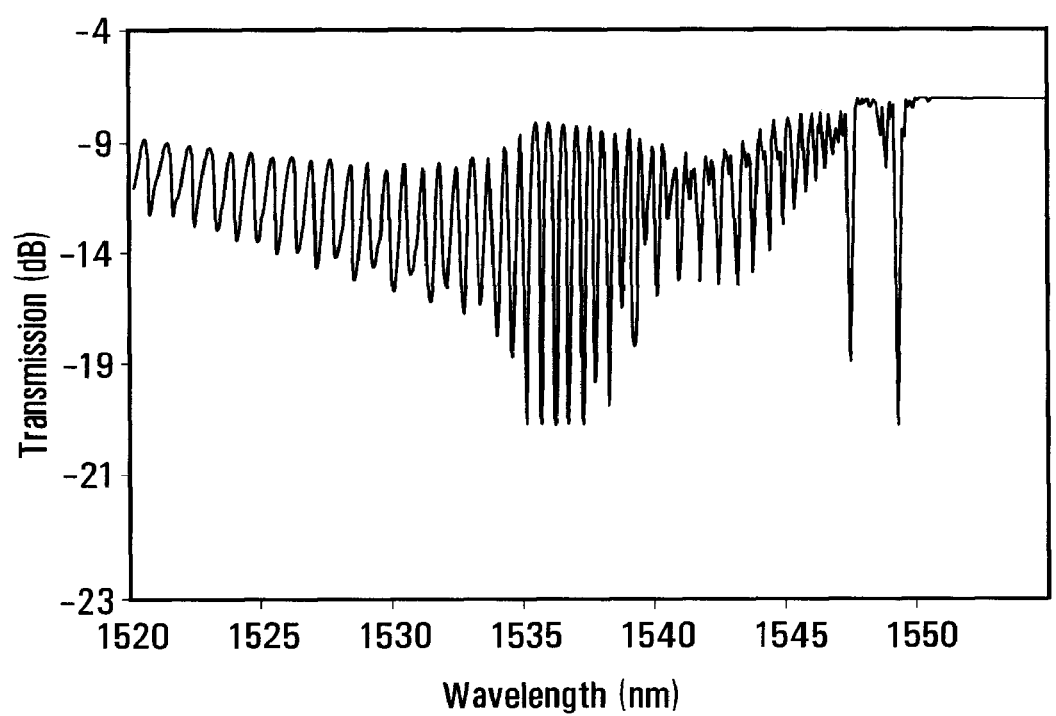
FIG. 12 is a graph showing the transmission spectrum of gold-plated TFBG in a sugar solution. The bracket identifies the peak position of the anomalous resonance.
Figure 13:
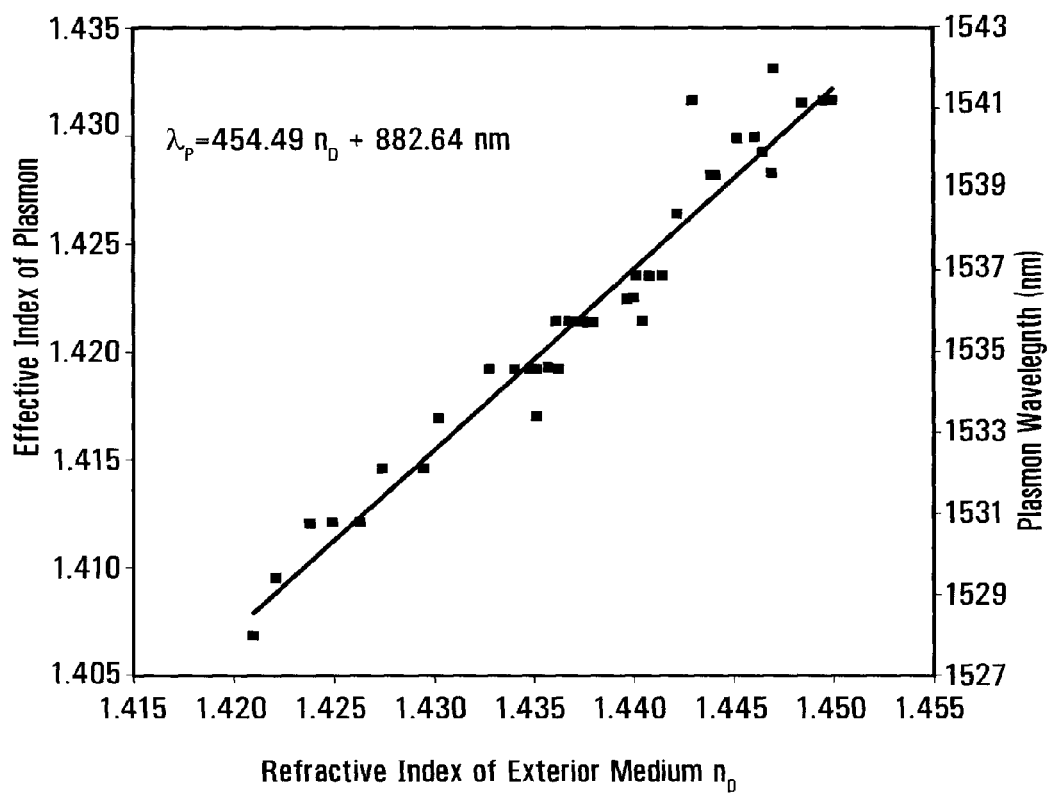
FIG. 13 is a graph showing the SPR peak wavelength ($\lambda_p$) and corresponding cladding mode effective index on the refractive index of the external medium at 589 nm ($n_D$)

After the gold deposition, the fiber transmission spectrum is visibly modified, but without measurable features of interest, as shown in FIG. 11, indicating that the very thin gold layer has had an effect. However, no narrowband SPR resonances can be seen in the wavelength spectrum sampled by the cladding modes. When the gold-coated grating is immersed in liquids with various refractive indices (sugar solutions), anomalous resonances appear for certain very specific sugar concentrations, as determined from Abbe refractometer measurements of the refractive index of the solutions at 589 nm (nD) (FIG. 12). The accuracy of the Abbe refractometer that was used is of ±0.0002. These resonances are not the same as those obtained for uncoated tilted fiber gratings, since they have a finite bandwidth within the cladding mode envelope and their maximum attenuation shifts rapidly with the external index. The peak position of the anomalous resonance ($\lambda_P$) is obtained by fitting the envelope of the cladding mode resonances. FIG. 13 shows how $\lambda_P$ changes as the refractive index of the outer medium is increased by small amounts. The spatial width of the envelope of the anomalous resonances is about 5 nm.

By using equation (1) to find the effective indices of the cladding modes within a resonance and the refractive index of silica near 1550 nm (n=1.444), it is possible to calculate the angular spread of the equivalent angles of incidences (since the effective index is equal to the projection on the fiber axis of the refractive index in silica). For the data of FIG. 12, the angular spread is 3.5 degrees (around a mean incidence angle θ=78°. This angle of incidence agrees with the predicted value for gold-coated silica glass in sucrose solutions interrogated at wavelengths close to 1500 nm. The angular spread of the resonance also corresponds well to typical values obtained for SPR measurements made with the Kretschmann configuration. Furthermore, the wavelength shift as a function of $n_D$ is well approximated by a straight line with a slope of 454 pm/($10^{-3}$ change in $n_D$). Even considering the dispersion of the sugar solutions between 589 nm and the 1520-1560 nm region, this is again in quantitative agreement with the expected behavior for contra-directional gratings in gold-coated silica fibers where shifts of the order of 100-500 pm/($10^{-3}$ change in $n_{ext}$) were theoretically predicted. These observations support the hypothesis that the resonance seen is indeed due to a SPR that is perturbing some of the cladding modes. In particular, the effective indices of the plasmons that are observed are smaller than the glass refractive index but corresponds to a situation where the plasmons are seen as perturbed cladding modes with a local electromagnetic field maximum at the outer metal boundary. It is this local field maximum that enhances the sensitivity of the cladding mode resonance to the exact value of external index.

The SPR waves can be used for chemical and biological monitoring through changes in the refractive index of the medium in which the fiber is located or through changes in the refractive index of the gold layer itself.

The tilted grating discussed above can be used for a number of different sensing applications, examples of which are discussed below:

1. Strain Gage with Thermal Compensation

As discussed earlier, the response of the tilted grating includes a core mode resonance component and a cladding mode resonance component. The core mode resonance component conveys the response of the sensor to temperature and elongation strain. In a specific example as the temperature of the grating changes or as elongation strain acts on the tilted grating the peak wavelength of the core mode resonance will shift. On the other hand, the wavelength gap between the peak wavelength of the core mode resonance and anyone of the peaks in the cladding mode resonance is generally constant with temperature. This means that as the temperature changes this gap will also change. However, if only elongation strain is applied on the sensor and the temperature is maintained constant the peaks of the core mode resonance component and of the cladding mode resonance components will shift in unison maintaining the gap constant. So, the gap change is indicative of the temperature variation only. Once the wavelength shift due only to temperature is determined, it suffices to subtract this wavelength shift from say the total wavelength shift of the main peak of the core mode resonance to determine the wavelength shift due only to elongation strain. Once this wavelength shift is known, the elongation strain can be derived easily.

Figure 14:
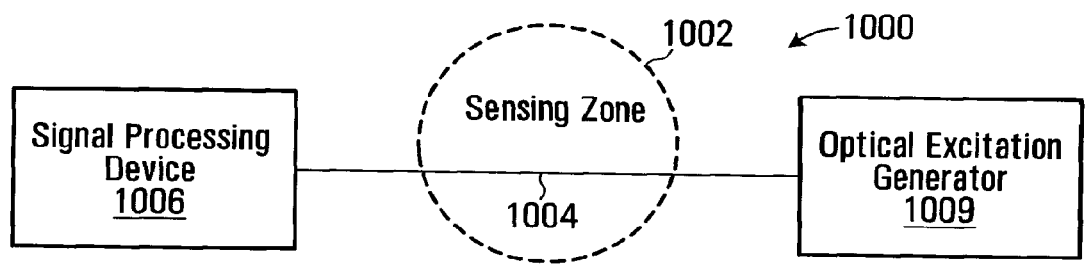
FIG. 14 is a block diagram of a measuring apparatus using a tilted grating, according to an example of implementation of the invention.

FIG. 14 shows a measurement apparatus 1000 using a titled grating. The measurement apparatus 1000 can be used to measure elongation strain, independent of temperature variations. The measurement is performed in a sensing zone 1002. Generally, the measurement apparatus 1000 has an optical sensor 1004 which is located in the sensing zone 1002 and includes a tilted grating, a signal processing device 1006 which performs an analysis of the optical response generated by the optical sensor 1004, and an optical excitation generator 1008 that injects into the optical sensor 1004 an optical excitation.

The sensing zone 1002 is the area where the measurement is to be made. The optical sensor 1004 has a continuous length of optical fiber. The optical fiber has a core in which is formed a TFBG.

In use, the optical excitation generator 1008 generates light which is injected into the optical fiber length that leads to the optical sensor 1004. The optical excitation reaches the TFBG which filters out from the optical excitation wavelengths corresponding to the peaks in the core and cladding mode resonances. The optical excitation that reaches the signal processing device 1006 is lacking the wavelengths filtered out by the TFBG. The signal processing device 1006 uses the information it receives from the optical sensor 1004 to derive the intensity of the elongation strain acting on the optical sensor 1004 in the sensing zone 1002, corrected for temperature variations in the sensing zone 1002. If desired to measure pressure or displacement acting on the optical sensor 1004, there may be a necessity to mount the optical sensor 1004 on a transducer structure (not shown in the drawings) that is directly exposed to pressure or displacement and communicates this pressure or displacement directly to the optical sensor 1004 in the form of elongation strain. Such transducer structures are known in the art and do not need to be discussed here in greater details.

Figure 18:
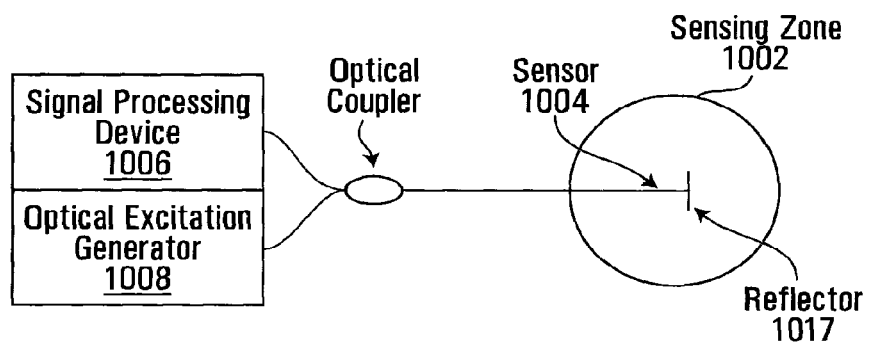
FIG. 18 is a block diagram of a measuring apparatus using a tilted grating, according to an example of implementation of the invention. The apparatus comprises a reflector as well as an optical coupler.

Note that different measurement apparatus architectures can be used. A variant is shown in FIG. 18, where the excitation and the collection of the TFBG response are made from the same side of the optical fiber. Specifically, in this embodiment, light generated by the optical generator 1008 is injected into the optical fiber length that leads to an optical coupler and to the optical sensor 1004. The optical excitation reaches the TFBG which filters out from the optical excitation wavelengths corresponding to the peaks in the core and cladding mode resonances. The optical fiber includes a reflector 1017 that will reflect back toward the signal processing device/optical excitation generator combination, the response produced by the TFBG. The reflector 1017 can be formed at a termination point of the optical fiber. In a specific example of implementation, the termination is a straight termination. Different mechanisms can be used to provide reflectivity at the reflector 1017. In one example, the reflectivity is achieved via Fresnel reflection. In a different example, the reflectivity is provided by a reflective coating deposited on the straight termination. In another possible example, the reflector 1017 is a non-tilted grating that has a reflection spectrum wide enough to overlap two or more of the cladding mode resonances produced by the tilted grating.

Another possibility is to form on the sensor a coating which expands in response to a certain substance or condition. The expansion causes elongation strain which can then indirectly either detect the substance or measure its concentration. The specification provides below examples of substances that respond to physical manifestations and that can induce a measurable strain on the sensor.

Figure 15:
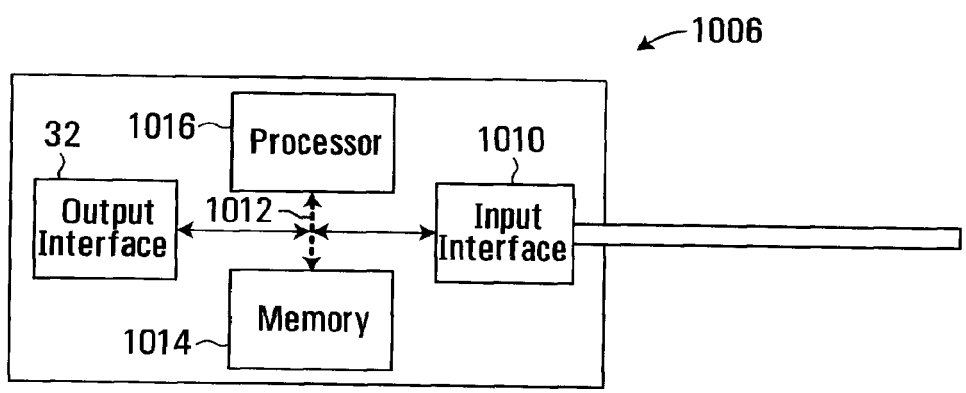
FIG. 15 is a block diagram of the signal processing device of the measurement apparatus shown in FIG. 14.

The signal processing device extracts from the response from the optical sensor 1004 information on the elongation strain acting on the optical sensor 1004 along with the temperature in the sensing zone 1002. FIG. 15 is a block diagram of the signal processing device 1006. The signal processing device 1006 is based on a computer platform that enables to perform digital signal processing on the response received from the optical sensor 1004 such as to derive the information desired. More specifically, the signal processing device 1006 includes in input interface 1010 that is coupled to the optical fiber length leading directly to the optical sensor 1004. The input interface 1010 will convert the signal into an electric digital signal, including performing appropriate filtering. The digital signal is then impressed on the data bus 1012 that establishes a communication path between a processor 1016 and a memory device 1014. The processor 1016 executes program code that processes the data in the digital signal to extract information on the elongation strain and temperature, according to the logic discussed above.

The signal processing device 1006 also has an output interface 1018 that allows communicating the result of the mathematical processing to an external entity. The external entity can be a human operator or a piece of equipment that uses the information generated by the signal processing device 1006 for specific purposes.

Accordingly, the measurement apparatus 1000 can measure the elongation strain acting on the optical sensor 1004 and the temperature in the sensing zone 1002.

2. Multi-Purpose Sensor

As discussed previously, the TBFG can be used to sense two or more physical manifestations. A senor can be provided to measure the index of refraction adjacent the sensing surface of the sensor, and another physical manifestation such as elongation strain and/or temperature. The measurement of the elongation strain and/or temperature was discussed earlier. The measurement of the index of refraction can be made in two different ways. One is to track a wavelength shift of the cladding mode resonances, as discussed in connection with FIGS. 2a and 2b. The other is to detect the occurrence of surface plasmon resonances, by determining which one of the cladding modes will experience loss, as discussed earlier.

3. Bending and Strain Gage and/or Temperature Sensor

Figure 16:
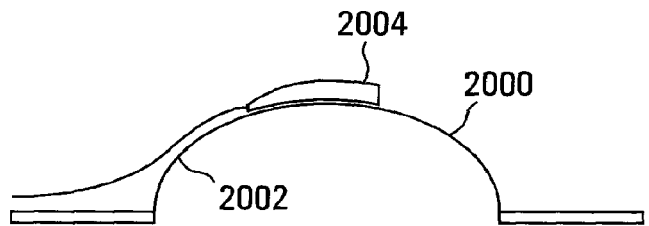
FIG. 16 is a scheme of a diaphragm 2000 that is made of flexible material and exposed to pressure on its side 2002. A sensor 2004 is mounted to the diaphragm. The sensor is placed on the convex side of the diaphragm 2000.
Figure 17:
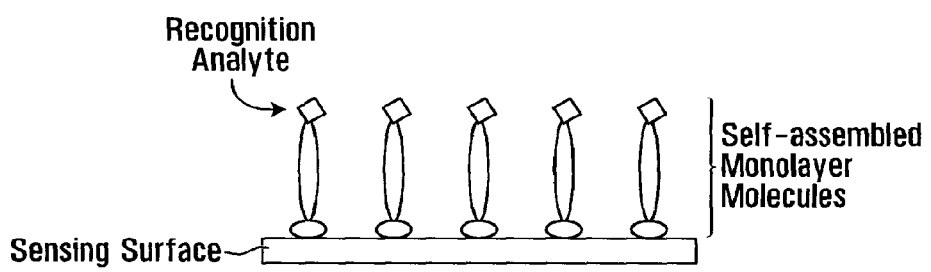
FIG. 17 is a schematic representation of self-assembled monolayers molecules on the sensing surface. The self-assembled monolayers molecules comprises a recognition analyte which associates with an analyte of interest.

As discussed earlier, the cladding mode resonances of the TFBG can be used to detect bending, in particular the low order cladding modes. Accordingly, by interrogating the TFBG in the wavelength that corresponds to those low order cladding modes, the degree of bending of the sensor can be determined. In a specific example, the power ratio of the first two resonances in the cladding mode varies with the degree of bending and can be used to accurately measure this parameter. At the same time the elongation strain and/or temperature can be measured by the techniques discussed earlier. The measurement of the degree of bending of the sensor can be used as an indirect measure of another physical manifestation which acts on the sensor to induce bending in it. For example, the sensor can be mounted on a diaphragm that is exposed to pressure. The degree of pressure determines the extent to which the diaphragm bows out. A sensor placed on the diaphragm will be caused to bend accordingly, and by measuring the degree of bending one can determine the extent to which the diaphragm bows and consequently the pressure acting on the diaphragm. This is shown in FIG. 16. The diaphragm 2000 that is made of flexible material is exposed to pressure on its side 2002. A sensor 2004 is mounted to the diaphragm. The sensor is placed on the convex side of the diaphragm 2000 but it can also be placed on the concave side as well.

Another possibility is to coat the sensor with a substance that induces bending in the sensor in response to a certain physical manifestation. For example, the coating can be placed only on one side of the sensor. The material of the coating is selected such that it swells when in contact with the substance to detect. When the coating swells it induces bending in the sensor which can be detected as indicated earlier. By properly selecting the coating the sensor can thus be made responsive to a wide variety of substances, such as humidity (water), chemical substances and biological substances.

In one example, the substances that would be responsive to water are, but not limited to, water-swellable materials.

The water-swellable material relates, for example, to a particulate absorbent material comprising a particulate core of absorbent polymers, coated with a coating agent, comprising or being an organic coating compound, which has one or more polar groups.

The absorbent polymer refers, for example, to a polymer, which is water-insoluble, water-swellable or gelling. These polymers are typically lightly cross-linked polymers, which contain a multiplicity of acid functional groups such as carboxylic acid groups. Examples of acid polymers suitable for use herein include those which are prepared from polymerizable, acid-containing monomers, or monomers containing functional groups which can be converted to acid groups after polymerization. Thus, such monomers include olefinically unsaturated carboxylic acids and anhydrides, and mixtures thereof. The acid polymers can also comprise polymers that are not prepared from olefinically unsaturated monomers.

Examples of such polymers include, but are not limited to, polysaccharide-based polymers such as carboxymethyl starch and carboxymethyl cellulose, and poly(amino acid) based polymers such as poly(aspartic acid).

Some non-acid monomers can also be included, usually in minor amounts, in preparing the absorbent polymers herein. Such non-acid monomers can include, for example, but not limited to, monomers containing the following types of functional groups: carboxylate or sulfonate esters, hydroxyl groups, amide-groups, amino groups, nitrile groups, quaternary ammonium salt groups, and aryl groups (e.g., phenyl groups, such as those derived from styrene monomer). Other optional non-acid monomers include unsaturated hydrocarbons such as ethylene, propylene, 1-butene, butadiene, and isoprene.

Olefinically unsaturated carboxylic acid and anhydride monomers useful herein include the acrylic acids typified by acrylic acid itself, methacrylic acid, .alpha.-chloroacrylic acid, a-cyanoacrylic acid, .beta.-methylacrylic acid (crotonic acid), .alpha.-phenylacrylic acid, .beta.-acryloxypropionic acid, sorbic acid, .alpha.-chlorosorbic acid, angelic acid, cinnamic acid, p-chlorocinnamic acid, .beta.-stearylacrylic acid, itaconic acid, citroconic acid, mesaconic acid, glutaconic acid, aconitic acid, maleic acid, fumaric acid, tricarboxyethylene, and maleic anhydride.

In one specific example, the absorbent polymers contain carboxyl groups. These polymers include hydrolyzed starch-acrylonitrile graft copolymers, partially neutralized hydrolyzed starch-acrylonitrile graft copolymers, starch-acrylic acid graft copolymers, partially neutralized starch-acrylic acid graft copolymers, hydrolyzed vinyl acetate-acrylic ester copolymers, hydrolyzed acrylonitrile or acrylamide copolymers, slightly network cross linked polymers of any of the foregoing copolymers, polyacrylic acid, and slightly network cross linked polymers of polyacrylic acid. These polymers can be used either solely or in the form of a mixture of two or more different polymers.

Those of skills in the art will be familiar with the process of coating the water-swellable material onto the sensor.

In a further example, the water-swellable material includes, but is not limited to, clay intimately mixed with a polypropene, a polybutene or a mixture of polypropene and polybutene, and a clay binding ion-exchange or coupling agent compound, to provide a composition having an unexpected capacity for swelling upon contact with water. The composition should include a clay binder that is ion-exchanged with clay platelet cations on internal negative charge sites of the clay platelets, or reacted with hydroxyl moieties at the clay platelet edges to achieve unexpected water-swellability.

The water-swellable clay utilized can be, but not limited to, any water-swellable layered material, such as a smectite clay, which will swell upon contact with water. The clay may be smectite clay, such as a montmorillonite or a bentonite clay. This clay has sodium as a predominant exchange cation. However, the clay utilized may also contain other cations such as magnesium and iron.

Those skilled in the art will be familiar with the methods for preparation of the compositions described herein.

4. Chemical/Biological Sensor

The sensor using a TFBG uses an interface responsive to the biological or chemical element to be detected to produce a physical manifestation that can be measured by the sensor. The interface can be designed to impress on the sensor a physical force which can be directly measured. An example of such interface was mentioned earlier and it would typically be in the form of a coating that causes the sensor to bend or stretch when it comes in contact with the biological or chemical element to be detected.

The interface can also be such as to cause SRI changes in response to the presence of the biological or chemical element to be detected. The chemical or biological sensor can also function without the need of an interface detects SRI changes which can be used in applications where a direct measure of the SRI is required or applications where the SRI change is an indicator of the occurrence of a chemical or a biological process or element. As briefly mentioned above, the SRI can be measured in two different manners. One involves tracking the wavelength shift by of the cladding mode resonances, as discussed in connection with FIGS. 2 (a) and 2 (b). The other uses the detection of SPR.

The sensor can be used as a chemical sensor to detect changes in SRI caused by the presence of a chemical element such that, but not limited to, the sensor can be used for determining the concentration of sugar in a medium, such as an aqueous solution, for determining the concentration of alcohol in a medium, for measuring the degree of curing of an adhesive, as the adhesive cures the SRI changes. By measuring the SRI one can track the degree of curing or detect a threshold at which the adhesive is considered to be cured. The invention is also used for measuring the degree of curing of cement in a fashion similar to the curing of an adhesive. The invention is further used as a biological detector. Generally, the biological detector includes an interface.

As used herein, the term chemical or biological analyte refers to a chemical or biological element to be detected.

The chemical and biological analytes that are contemplated include, but are not limited to, bacteria; yeasts; fungi; viruses; rheumatoid factor; antibodies, including, but not limited to IgG, IgM, IgA and IgE antibodies; carcinoembryonic antigen; *streptococcus* Group A antigen; antigen; viral antigens; antigens associated with autoimmune disease; allergens; tumor antigens; *streptococcus* Group B antigen, HIV I or HIV II antigen; or host response (antibodies) to these and other viruses; antigens specific to RSV or host response (antibodies) to the virus; an antibody; antigen; enzyme; hormone; polysaccharide; protein; prions; lipid; carbohydrate; drug; nucleic acid; *Salmonella* species; *Candida* species, including, but not limited to *Candida albicans* and *Candida tropicalis; Salmonella* species; *Neisseria meningitides* groups A, B, C, Y and W sub 135, *Streptococcus pneumoniae; E. coli* K1. *E. coli; Haemophilus influenza* type B; an antigen derived from microorganisms; a hapten; a drug of abuse; a therapeutic drug; environmental agents; and antigens specific to Hepatitis; an enzyme; a DNA fragment; an intact gene; a RNA fragment; a small molecule; a metal; a toxin; a nucleic acid; a cytoplasm component; pili or flagella component; or any other analytes.

The analyte of interest would typically be in a carrier medium which can be solid, gel-like, liquid or gas. For instance analyte can be detected in a bodily fluid such as mucous, saliva, urine, fecal analyte, tissue, marrow, cerebral spinal fluid, serum, plasma, whole blood, sputum, buffered solutions, extracted solutions, semen, uro-genital secretion, pericardial, gastric, peritoneal, pleural, throat swab, subfractions thereof, or other washes and the like. A gaseaous medum may be, but not limited to, air.

An aqueous buffered solution may be employed to dilute the analyte, such an aqueous buffer solution may be lightly or heavily buffered depending on the nature of the analyte to be detected. Various buffers may be employed such as carbonate, phosphate, borate, Tris, acetate, barbital, Hepes, or the like. Organic polar solvents, e.g., oxygenated neutral solvents, may be present in amounts ranging from about 0 to 40 volume percent such as methanol, ethanol, .alpha.-propanol, acetone, diethylether, or the like.

In one specific example, the interface has a recognition analyte that can be attached on the sensing surface of the sensor and will associate with the analyte of interest (FIG. 1). When such binding occurs the SRI changes. The change is specific in that the SRI acquires a specific value which indicates that the binding has taken place. The cladding mode resonances "interrogate" the electric/dielectric interface and when the SRI acquires the specific value, the energy in at least one of the resonance will be transferred into a SPR. The energy transfer will show as a reduced power in that particular cladding mode resonance, allowing determining that the SRI is at the specific value indicative of a binding event. Note that since several resonances interrogate the electric/dielectric interface, this technique can at least in theory monitor simultaneously for a set of different specific SRI values, each associated to a given resonance in the cladding mode resonance component. As such, several binding events, corresponding to different SRI values, can be detected simultaneously.

The recognition analyte is thus a component of a specific binding pair and includes, but is not limited to, antigen/antibody, enzyme/substrate, oligonucleotide/DNA, chelator/metal, enzyme/inhibitor, bacteria/receptor, virus/receptor, hormone/receptor, DNA/RNA, or RNA/RNA, oligonucleotide/RNA, and binding of these species to any other species, as well as the interaction of these species with inorganic species.

The recognition analyte that is attached to the sensing surface can be, but is not limited to, toxins, antibodies, antigens, hormone receptors, parasites, cells, haptens, metabolizers, allergens, nucleic acids, nuclear analytes, autoantibodies, blood proteins, cellular debris, enzymes, tissue proteins, enzyme substrates, coenzymes, neuron transmitters, viruses, viral particles, microorganisms, proteins, polysaccharides, chelators, drugs, and any other member of a specific binding pair. The recognition analyte is specifically designed to associate with the analyte of interest.

The recognition analyte may be passively adhered to the sensing surface. If required, the recognition analyte may be covalently attached to the sensing surface of the sensor. The chemistry for attachment of recognition analyte is well known to those skilled in the art.

Recognition analyte for detection of bacteria may have binding activity to specifically bind a surface membrane component, protein or lipid, a polysaccharide, a nucleic acid, or an enzyme. The analyte, which is specific to the bacteria, may be a polysaccharide, an enzyme, a nucleic acid, a membrane component, or an antibody produced by the host in response to the bacteria. The presence of the analyte may indicate an infectious disease (bacterial or viral), cancer or other metabolic disorder or condition. The presence of the analyte may be an indication of food poisoning or other toxic exposure. The presence of the analyte may also be an indication of bacterial contamination.

A wide range of techniques can be used to apply the recognition analyte of the interface to the sensing surface of the sensor. The sensing surface may be, for example but not limited to, coated with recognition analyte by total immersion in a solution for a predetermined period of time; application of solution in discrete arrays or patterns; spraying, ink jet, or other imprinting methods; or by spin coating from an appropriate solvent system. The technique selected should minimize the amount of recognition analyte required for coating a large number of test surfaces and maintain the stability/functionality of recognition analyte during application.

Attachment of the Recognition Analyte by Self-Assembled Monolayers on Sensing Surface In a further embodiment, the invention includes attachment of the recognition analyte into the surface or the interior of the sensing surface, through self-assembled monolayers.

Self-assembled monolayers can be prepared using different types of molecules and different substrates. Commonly used examples are, but not limited to, alkylsiloxane monolayers, fatty acids on oxidic materials and alkanethiolate monolayers. This type of self-assembled monolayers holds great promise for applications in several different areas. Some examples of suggested and implemented applications are, but not limited to, molecular recognition, self-assembly monolayers as model substrates and biomembrane mimetics in studies of biomolecules at surfaces, selective binding of enzymes to surfaces.

There are many different systems of self-assembling monolayers based on different organic components and supports, such as, but not limited to, systems of alkanethiolates, $HS(CH_2)_n R$, on gold layers. The alkanethiols chemisorb on the gold surface from a solution in which the gold layer is immersed, and form adsorbed alkanethiolates with loss of hydrogen. Adsorption can also occur from the vapor. Self-assembling monolayers formed on gold from long-chain alkanethiolates of structure $X(CH_2)_n Y(CH_2)_m S$ are highly ordered. A wide variety of organic functional groups (X,Y) can be incorporated into the surface or interior of the monolayer.

In one example, the self-assembling monolayer is formed of a carboxy-terminated alkane thiol stamped with a patterned elastomeric stamp onto a gold surface. The alkanethiol is inked with a solution of alkanethiol in ethanol, dried, and brought into contact with a surface of gold. The alkanethiol is transferred to the surface only at those regions where the stamp contacts the surface, producing a pattern of self-assembling monolayer which is defined by the pattern of the stamp. Optionally, areas of unmodified gold surface next to the stamped areas can be rendered hydrophobic by reaction with a methyl-terminated alkane thiol. The details of the method are well known in the art.

The present invention, the self-assembling monolayer has the following general formula: X is reactive with metal or metal oxide. For example, X may be asymmetrical or symmetrical disulfide (—R'SSY', —RSSY), sulfide (—R'SY', —RSY), diselenide (—R'Se—SeY'), selenide (—R'SeY', —RSeY), thiol (—SH), nitrile (—CN), isonitrile, nitro (—NO$_2$), selenol (—SeH), trivalent phosphorous compounds, isothiocyanate, xanthate, thiocarbamate, phosphine, thioacid or dithioacid, carboxylic acids, hydroxylic acids, and hydroxamic acids.

R and R' are hydrocarbon chains which may optionally be interrupted by hetero atoms and which are preferably non-branched for the sake of optimum dense packing. At room temperature, R is greater than or equal to seven carbon atoms in length, in order to overcome natural randomizing of the self-assembling monolayer. At colder temperatures, R may be shorter. In one embodiment, R is —(CH$_2$)$_n$— where n is between 10 and 12, inclusive. The carbon chain may optionally be perfluorinated. A person skilled in the art will understand that the carbon chain may be of any length.

Y and Y' may have any surface property of interest. For example, Y and Y' could be any among the great number of groups used for immobilization in liquid chromatography techniques, such as hydroxy, carboxyl, amino, aldehyde, hydrazide, carbonyl, epoxy, or vinyl groups.

Self-assembling monolayers of alkyl phosphonic, hydroxamic, and carboxylic acids may also be useful for the methods of the present invention. Since alkanethiols do not adsorb to the surfaces of many metal oxides, carboxylic acids, phosphonic acids, and hydroxamic acids may be preferred for X for those metal oxides.

R may also be of the form $(CH_2)_a$—Z—$(CH_2)_b$, where a.gtoreq.0, B.gtoreq.7, and Z is any chemical functionality of interest, such as sulfones, urea, lactam, and the like.

The stamp may be applied in air, gel, semi-gel, or under a fluid, such as water to prevent excess diffusion of the alkanethiol. For large-scale or continuous printing processes, it is most desirable to print in air, since shorter contact times are desirable for those processes.

In one specific example the sensor can be used in immunoassay methods for either antigen or antibody detection. The sensors may be adapted for use in direct, indirect, or competitive detection schemes, for determination of enzymatic activity, and for detection of small organic molecules such as, but not limited to drugs of abuse, therapeutic drugs, environmental agents), as well as detection of nucleic acids and microorganisms.

For immunoassays, an antibody may serve as the recognition analyte or it may be the analyte of interest. The recognition analyte, for example an antibody or an antigen, should form a stable, dense, reactive layer on the attachment layer of the test sensor. If an antigen is to be detected and an antibody is the recognition analyte, the antibody should be specific to the antigen of interest; and the antibody (recognition analyte) should bind the antigen (analyte) with sufficient avidity that the antigen is retained at the surface of the sensing surface. In some cases, the analyte may not simply bind the recognition analyte, but may cause a detectable modification of the recognition analyte to occur. This interaction could cause an increase in mass at the test surface or a decrease in the amount of recognition analyte on the test surface. An example of the latter is the interaction of a degradative enzyme or analyte with a specific, immobilized substrate. In this case, one would see a diffraction pattern before interaction with the analyte of interest, but the diffraction pattern would disappear if the analyte were present.

In another specific example, the sensor applies to detection of nucleic acid molecules and nucleic acid probes. Nucleic acids can be attached to sensing surfaces in an hybridization assays. A sensing surface such as gold is modified with nucleic acids via for example, but not limited to, linkers, and blocking moieties, which serve to shield the nucleic acids from the sensing surface.

"Blocking moieties" are molecules which are attached to the sensing solid support and function to shield the nucleic acids from the sensing surface. For the purposes of this invention, the attachment of a sulfur moiety to a sensing surface, such as gold, is considered covalent.

By "nucleic acids" or "oligonucleotides" herein is meant at least two nucleotides covalently linked together. A nucleic acid of the present invention will generally contain phosphodiester bonds, although in some cases, as outlined below, a nucleic acid analogs are included that may have alternate backbones, comprising, for example, phosphoramide, phosphorothioate, phosphorodithioate, O-methylphophoroamidite linkages and peptide nucleic acid backbones and linkages.

The nucleic acids of the invention may also be characterized as "probe" nucleic acids and "target" nucleic acids. These terms are known in the art. Either probe or target nucleic acids may be attached to the solid support via linker. In a preferred embodiment, the probe nucleic acids are attached, via linker moieties, to the solid support, and the target nucleic acids are added in solution. The nucleic acid and the probe may be labeled.

Probe nucleic acids or probe sequences are preferably single stranded nucleic acids. The probes of the present invention are designed to be complementary to the target sequence, such that hybridization of the target sequence and the probes of the present invention occur. This complementarity need not be perfect; there may be any number of base pair mismatches which will interfere with hybridization between the target sequence and the single stranded probe nucleic acids of the present invention. However, if the number of mutations is so great that no hybridization can occur under even the least stringent of hybridization conditions, the sequence is not a complementary target sequence.

It will be appreciated by those in the art, the length of the probe will vary with the length of the target sequence and the hybridization and wash conditions.

In a possible variant, the nucleic acid is attached to the sensing surface in monolayers. The techniques to attach nucleic acid molecules to the sensing surface will be well known to those skilled in the art.

"Target nucleic acids" or "sequences" means a nucleic acid sequence on a single strand of nucleic acid. The target sequence may be a portion of a gene, a regulatory sequence, genomic DNA, cDNA, mRNA, or others. It may be any length, with the understanding that longer sequences are more specific. As is outlined herein, probes are made to hybridize to target sequences to determine the presence or absence of the target sequence in a sample. Target nucleic acids may be prepared or amplified as is commonly known in the art. When target nucleic acids are attached to the sensing surface, they will generally be the same size as outlined for probe nucleic acids, above.

In general, blocking moieties have at least a first and a second end. The first end is used to covalently attach the blocking moiety to the sensing surface. The second end terminates in a terminal group, defined below. However, in some embodiments, the blocking moieties may be branched molecules. Thus, for example, the first end is used for attachment to the solid support and all or some of the other ends may terminate in a terminal group, as defined below.

The second end of the blocking moiety terminates in a terminal group. By "terminal group" or "terminal moiety" herein is meant a chemical group at the terminus of the blocking moiety. The terminal groups may be chosen to modulate the interaction between the nucleic acid and the blocking moieties, or the surface. Thus, for example, in another embodiment, when the blocking moieties form a monolayer as is generally described below, the terminal group may be used to influence the exposed surface of the monolayer. Thus, for example, the terminal group may be neutral, charged, or sterically bulky. For example, the terminal groups may be negatively charged groups, effectively forming a negatively charged surface such that when the probe or target nucleic acid is DNA or RNA the nucleic acid is repelled or prevented from lying down on the surface, to facilitate hybridization. This may be particularly useful when the nucleic acid attached to the sensing surface via a linker moiety is long.

In addition to the blocking moieties, the sensing surface of the invention comprises modified nucleic acids.

The nucleic acids of the invention are modified with linker moieties, to form modified nucleic acids which are attached to the sensing surface. By "modified nucleic acid" herein is meant a nucleic acid as defined above covalently attached to a linker moiety.

By "linker moieties" is meant molecules which serve to immobilize the nucleic acid at a distance from the sensing surface. Linker moieties have a first and a second end. The first end is used to covalently attach the linker moiety to the sensing surface. The second end is used for attachment to the nucleic acid.

The blocking moieties are made using techniques well known in the art.

In a further variant, the present invention is useful in methods of assaying for the presence or absence of target nucleic acids in the sample to be analyzed. Thus, the present invention provides methods of hybridizing probe nucleic acids to target nucleic acids. The methods comprise adding or contacting target nucleic acids to a sensing surface of the invention. The sensing surface comprises blocking moieties, and modified probe nucleic acids. The contacting is done under conditions where the probe and target nucleic acids, if suitably complementary, will hybridize to form a double-stranded hybridization complex.

The assay conditions may vary, as will be appreciated by those in the art, and include high, moderate or low stringency conditions as is known in the art. The assays may be done at a variety of temperatures, and using a variety of incubation times, as will be appreciated by those in the art. In addition, a variety of other reagents may be included in the hybridization assay, including buffers, salts, proteins, detergents or the like. Positive and negative controls are generally run.

In a further specific example, the sensor is used to detect microorganisms in medium.

The term "microorganism" as used herein means an organism too small to be observed with the unaided eye and includes, but is not limited to bacteria, a cell, cells, viruses, protozoans, fungi, and ciliates.

In another embodiment, microorganisms such as, but not limited to, bacteria, bacteriophages, viruses, and cellular analyte can be detected by sampling the nucleic acids, such as, but not limited to, nucleotides or polynucleotides that they contain or release. Microorganisms can also be detected by sampling the protein, carbohydrates and/or lipids that they contain or release.

In a possible variant, the microorganims may be detected by a recognition analyte such as not limited to an antibody assembled as a monolayer on the sensing surface or may be detected by interacting directly on the bare sensing surface.

The embodiments of the invention described herein can be used in several application areas, for example, but not limited to, for the quantitative or qualitative determination of chemical, biochemical or biological analytes in screening assays in pharmacological research, for real-time binding studies or in the determination of kinetic parameters in affinity screening or in research, for DNA and RNA analytics and for the determination of genomic or proteomic differences in the genome, for the determination of protein-DNA interactions, for the determination of regulation mechanisms for mRNA expression and protein (bio)synthesis, for the determination of biological or chemical markers, such as mRNA, proteins, peptides or low molecular organic (messanger) compounds, for the determination of antigens, pathogens or bacteria in pharmacological product research and development, for therapeutic drug selection, for the determination of pathogens, harmful compounds or germs, such as, but not lifted to, *salmonella*, prions, viruses and bacteria.

Although various embodiments have been illustrated, this was for the purpose of describing, but not limiting, the invention. Various modifications will become apparent to those skilled in the art and are within the scope of this invention, which is defined more particularly by the attached claims.

The invention claimed is:

1. A pressure sensor, comprising:
    a) a flexible member, flexing in response to a pressure differential acting across said flexible member;
    b) an optical pathway coupled to said flexible member, said optical pathway including a core and a cladding;
    c) a tilted grating in said optical pathway, said flexible member imparting a bending deformation to said tilted grating when said flexible member flexes, said tilted grating being responsive to electromagnetic radiation propagating in the optical pathway to induce a propagation of cladding mode electromagnetic waves conveying bending information on the bending deformation imparted to said tilted grating; and
    d) an output for generating a signal conveying pressure data, the signal derived from at least the information on the bending deformation imparted to said tilted grating.

2. Pressure sensor as defined in claim 1, wherein said optical pathway includes an optical fiber.

3. Pressure sensor as defined in claim 1, wherein a response of said tilted grating includes a core mode resonance component and a cladding mode resonance component.

4. Pressure sensor as defined in claim 1, wherein said tilted grating is a tilted Bragg grating.

* * * * *